(12) United States Patent
Martinmäki et al.

(10) Patent No.: US 10,993,656 B2
(45) Date of Patent: May 4, 2021

(54) MEASURING AND ESTIMATING SLEEP QUALITY

(71) Applicant: Polar Electro Oy, Kempele (FI)

(72) Inventors: Kaisu Martinmäki, Oulu (FI); Topi Korhonen, Oulu (FI); Kari Säynäjäkangas, Kempele (FI); Nuutti Santaniemi, Kempele (FI); Tero Posio, Oulu (FI); Pertti Puolakanaho, Kiviniemi (FI); Elias Pekonen, Oulu (FI)

(73) Assignee: Polar Electro Oy, Kempele (FI)

( * ) Notice: Subject to any disclaimer, the term of this patent is extended or adjusted under 35 U.S.C. 154(b) by 92 days.

(21) Appl. No.: 15/903,954

(22) Filed: Feb. 23, 2018

(65) Prior Publication Data
US 2018/0242902 A1 Aug. 30, 2018

(30) Foreign Application Priority Data
Feb. 27, 2017 (EP) ..................................... 17158093

(51) Int. Cl.
*A61B 5/04* (2006.01)
*A61B 5/00* (2006.01)
(Continued)

(52) U.S. Cl.
CPC ........ *A61B 5/4815* (2013.01); *A61B 5/02438* (2013.01); *A61B 5/0402* (2013.01);
(Continued)

(58) Field of Classification Search
CPC . A61B 5/4815; A61B 5/02438; A61B 5/2444; A61B 5/2427; A61B 5/245;
(Continued)

(56) References Cited

U.S. PATENT DOCUMENTS

| 2005/0085738 A1 | 4/2005 | Stahmann et al. |
| 2010/0099954 A1 | 4/2010 | Dickinson et al. |

(Continued)

FOREIGN PATENT DOCUMENTS

| EP | 2278508 A1 * | 1/2011 | ........... A47C 31/123 |
| EP | 2278508 A1 | 1/2011 | |
| WO | 2016108751 A1 | 7/2016 | |

OTHER PUBLICATIONS

European Search Report for corresponding Application No. EP 17 15 8093, 3 pages, dated Aug. 30, 2017.

*Primary Examiner* — Allen Porter
*Assistant Examiner* — Adreanne A. Arnold
(74) *Attorney, Agent, or Firm* — FisherBroyles, LLP

(57) ABSTRACT

A computer-implemented method estimates sleep quality of a user. A related computer system, a computer program product, and a data structure are also described. The method includes receiving measurement data measured by at least one sensor device during a time interval; detecting from the measurement data one or more restless sleep signal patterns indicating a restless sleep interval longer than a first threshold duration and computing a number of the detected one or more restless sleep signal patterns; detecting, from the measurement data, one or more continuous sleep intervals not including any one of the one or more restless sleep signal patterns within a time interval longer than a second threshold duration and computing a total length of the one or more continuous sleep intervals; computing a sleep quality metric as a function of the number of the detected one or more restless sleep signal patterns and the total length of the detected one or more continuous sleep intervals, wherein the sleep quality metric indicates a quality of the user's sleep during the time interval; and outputting the sleep quality metric.

23 Claims, 8 Drawing Sheets

(51) Int. Cl.
  *A61B 5/18* (2006.01)
  *A61B 5/024* (2006.01)
  *A61B 5/11* (2006.01)
  *A61B 5/0402* (2006.01)
  *A61B 5/0476* (2006.01)

(52) U.S. Cl.
  CPC .......... *A61B 5/0476* (2013.01); *A61B 5/1118* (2013.01); *A61B 5/18* (2013.01); *A61B 5/4809* (2013.01); *A61B 5/4812* (2013.01)

(58) Field of Classification Search
  CPC ... A61B 5/0402; A61B 5/0476; A61B 5/1118; A61B 5/18; A61B 5/4809; A61B 5/4812
  See application file for complete search history.

(56) References Cited

U.S. PATENT DOCUMENTS

| | | |
|---|---|---|
| 2014/0088373 A1 | 3/2014 | Phillips et al. |
| 2016/0256741 A1 | 9/2016 | Holma et al. |
| 2017/0053513 A1 | 2/2017 | Savolainen et al. |
| 2017/0347948 A1* | 12/2017 | Thein .................. A61B 5/4812 |
| 2018/0242902 A1* | 8/2018 | Martinmaki ......... A61B 5/0402 |

* cited by examiner

MEASURING AND ESTIMATING SLEEP QUALITY

CROSS-REFERENCE TO RELATED APPLICATION

This application claims benefit to European Application No. 17158093.9, filed Feb. 27, 2017, which is incorporated by reference herein in its entirety.

BACKGROUND

Field

The present invention relates to a field of measuring a human and, in particular, to evaluating sleep quality through measurements.

Description of the Related Art

Modern activity monitoring devices sometimes called activity trackers employ motion sensors to measure user's motion during the day. Some activity monitoring devices may employ other sensors such as physiological or biometric sensors such as heart activity sensors. Some activity monitoring devices are also capable of estimating a sleep time and/or sleep quality of the user.

Continuity of the sleep has been shown to have a significant effect on a restorative value of the sleep. Therefore, it would be advantageous to provide a metric for estimating the continuity of the sleep such that it reflects the restorative value accurately.

SUMMARY

The present invention is defined by the subject matter of the independent claims.

Embodiments are defined in the dependent claims.

BRIEF DESCRIPTION OF THE DRAWINGS

In the following the invention will be described in greater detail by means of preferred embodiments with reference to the accompanying drawings, in which.

DETAILED DESCRIPTION

The following embodiments are exemplifying. Although the specification may refer to "an", "one", or "some" embodiment(s) in several locations of the text, this does not necessarily mean that each reference is made to the same embodiment(s), or that a particular feature only applies to a single embodiment. Single features of different embodiments may also be combined to provide other embodiments.

Figure 1:
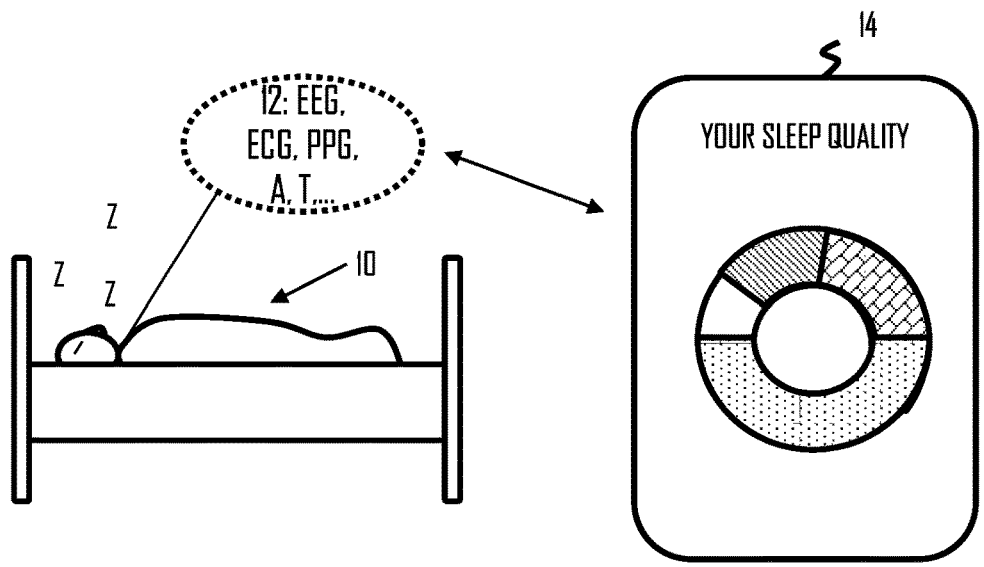
FIG. 1 illustrates a scenario to which embodiments of the invention may be applied.

FIG. 1 illustrates an example of a scenario to which embodiments of the invention may be applied. A system according to an embodiment of the invention comprises at least a processing circuitry configured to analyse measurement data measured from a user 10 during sleep. The processing circuitry may be realized in a wearable computer worn by the user, such as a smart watch. The processing circuitry may be realized in a portable electronic device 14 such as a smart phone or a tablet computer. The processing circuitry may be realized in a server computer such as a cloud server.

The measurement data may be provided by at least one sensor device operational at least during the sleep and configured to measure the user during the sleep. The sensor device(s) may measure one or more of the following features from the user: motion, electrocardiogram (ECG), photoplethysmogram (PPG), electroencephalography (EEG), bioimpedance, galvanic skin response, body temperature, respiration, electrooculography (EOG), or ballistocardiogram (BCG). The motion may be measured by a sensor device comprising an inertial sensor such as an accelerometer and/or a gyroscope, and the output of such a sensor device is motion measurement data. A sensor device measuring ECG, PPG, or BCG may output heart activity measurement data. In the ECG measurements, one or more electrodes attached to the user's skin measure an electric property from the skin which, through appropriate signal processing techniques, is processed into an ECG signal. In some techniques, the heart activity data represents appearance of R waves of electric heart impulses. In the PPG measurements, a light emitted by a light emitter diode or a similar light source and reflected back from the user's skin is sensed by using a photo diode or a similar light sensing component. The sensed light is then converted into an electric measurement signal in the light sensing component and signal processing is used to detect desired signal components from the electric measurement signal. In the PPG, P waves may be detected which enables computation of a PP interval and a heart rate, for example. A sensor device measuring the EOG may output electric measurement data representing eye motion. Respiration may be measured by a special-purpose respiration sensor outputting respiratory rate, but the respiratory rate may be measured from the heart activity as well.

It has been discovered that each of the above-described features measurable by using the at least one sensor device is capable of representing different sleep states. For example, when the user 10 is in a deep sleep state, the motion is minimal, a heart rate is low, respiration rate is low, temperature is low, a spectrum of heart rate variability represents a signal pattern on one frequency, etc. On the other hand, when the sleep is interrupted and the user is sleeping restlessly, the motion increases, heart rate increases, respiration rate increases, temperature rises, the spectrum of heart rate variability represents a signal pattern on a different frequency, etc. By using the at least one sensor device and appropriate signal processing to detect signal patterns from the measurement data, it is possible to detect continuous deep sleep phases and interrupted sleep phases. Analysis of the continuous deep sleep phases and interrupted sleep phases enables estimation of the sleep quality by the processing circuitry, and the processing circuitry may then output the estimated signal quality to the user 10 through a user interface of the electronic device 14 housing the processing circuitry or through an external user interface.

Figure 2:
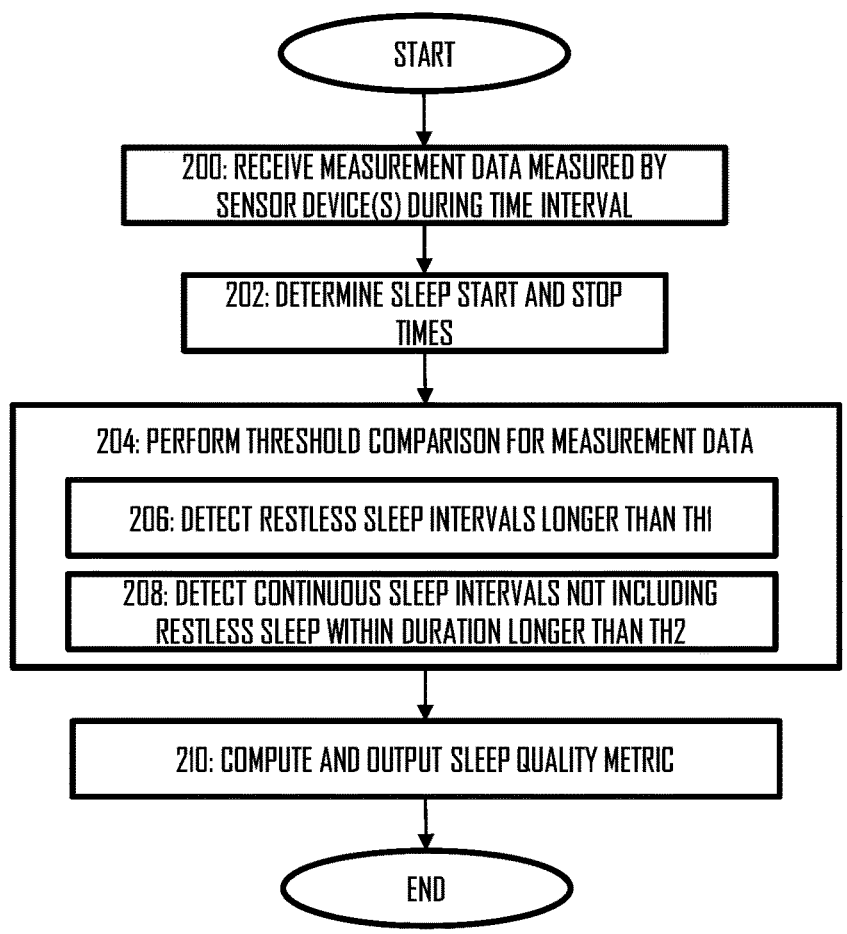
FIG. 2 illustrates a computer-implemented process for estimating sleep quality according to an embodiment of the invention.

FIG. 2 illustrates a method for estimating the sleep quality. The method may be computer-implemented and executed by the processing circuitry as a computer process defined by a computer program code of a suitable computer program product. Referring to FIG. 2, the process comprises: receiving measurement data measured by at least one sensor device during a time interval (block 200); determining a sleep start time and a sleep stop time in the measurement data (block 202); detecting from a subset of the measurement data, the subset measured between the sleep start time and the sleep stop time, one or more restless sleep signal patterns indicating a restless sleep interval longer than a first threshold duration and computing a number of the detected one or more restless sleep signal patterns (block 206); detecting, from the subset of the measurement data, one or more continuous sleep intervals not including any one of the one or more restless sleep signal patterns within a time interval longer than a second threshold duration and computing a total length of the one or more continuous sleep intervals (block 208); computing a sleep quality metric as a function of the number of the detected one or more restless sleep signal patterns and the total length of the detected one or more continuous sleep intervals, the sleep quality metric indicating a quality of the user's sleep during the time interval (block 210); and outputting the sleep quality metric (block 210).

The sleep quality metric may be output to the user through a user interface or to another device through a communication circuitry.

The method involves threshold comparison performed for the measurement data in block 204. The threshold comparison enables detection of relevant signal patterns that are associated with sleep states such as continuous sleep and restless sleep. Blocks 206 and 208 comprise certain embodiments of the threshold comparison for detecting the restless sleep phase (block 206) and the continuous sleep phase (block 208). The number of restless sleep intervals and the duration of the continuous sleep are both indicators of the overall sleep quality during a night, for example, and the processing circuitry may use both metrics in block 210 to obtain the sleep quality metric. In an embodiment, blocks 206 and 208 comprise using at least two thresholds in the detection of the restless sleep signal patterns (block 206) and the continuous sleep signal patterns (block 208). One of the thresholds is used for a quantity of the measurement data provided by the at least one sensor device, e.g. heart rate, acceleration or speed or another degree of motion, respiratory rate, bioimpedance, or a frequency of a signal pattern (in the heart rate variability, for example). Another one of the thresholds is a temporal threshold associated with time or duration.

In some embodiments, the subset measurement data may be received as such and there is no need to separately determine the sleep start time and the sleep stop time separately.

Figure 3:
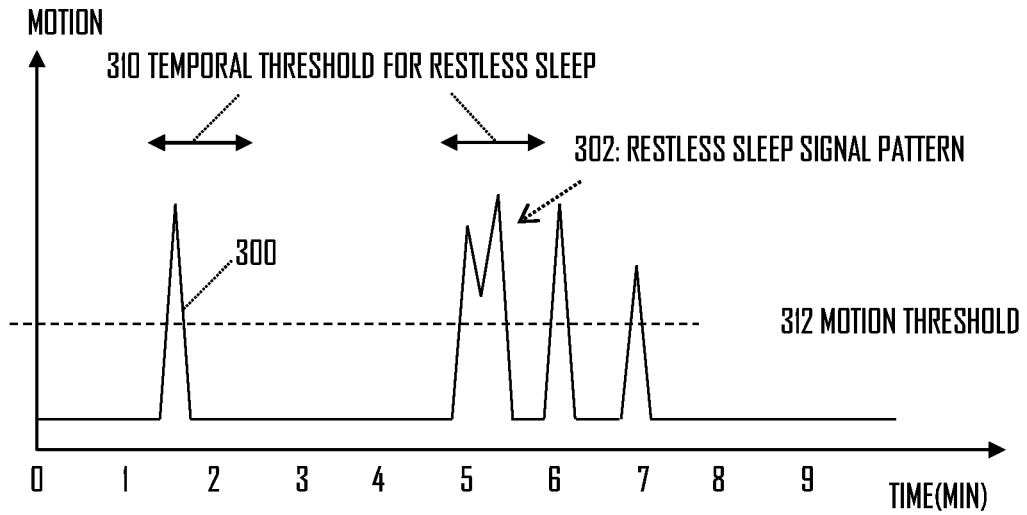
FIGS. 3 and 4 illustrate thresholds used when estimating sleep quality according to some embodiments of the invention.
Figure 4:
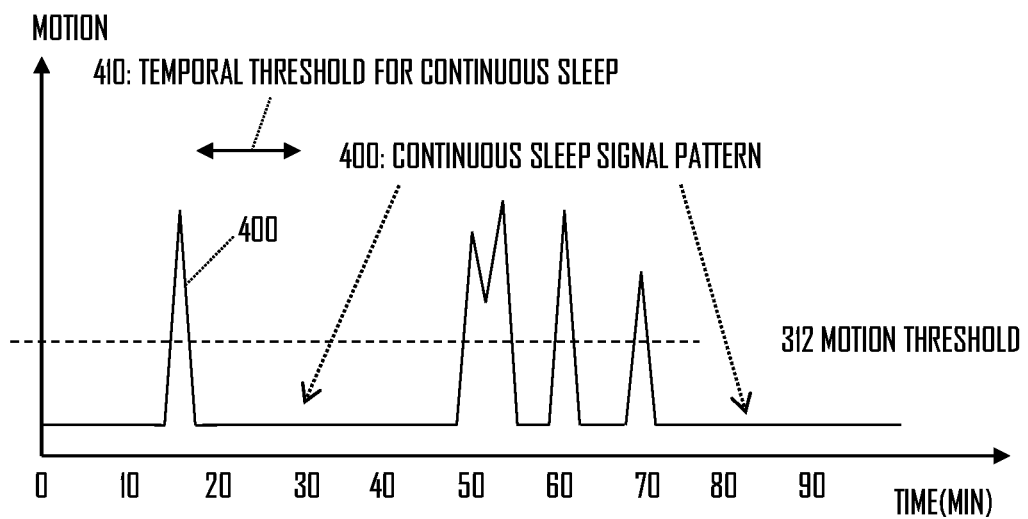

Let us now describe the threshold comparison in block 204 in greater detail with reference to embodiments of FIGS. 3 and 4. FIG. 3 illustrates an exemplary and simplified measurement signal measured by a motion sensor. Both FIGS. 3 and 4 illustrate a measurement signal in the form of a continuous line comprising peaks illustrating motion of the user 10 during the sleep. Let us assume that the measurement signal illustrated in FIGS. 3 and 4 represents the above-described subset of measurement data.

Referring to FIG. 3, block 206 is performed by using a motion threshold 312 used for distinguishing when the measurement signal represents motion above and below the threshold. The motion threshold may be set to such a level that the processing circuitry is capable of detecting user's movement by comparing the measurement signal with the threshold. When the measurement signal is above the motion threshold 312 (see the peaks in FIG. 3), the processing circuitry may determine that the user is moving. When the measurement signal is below the threshold, the processing circuitry may determine that the user is lying still.

A temporal threshold for restless sleep 310 is used for determining when the user is moving for such a long period that it may be considered as restless sleep. A single movement during the night may account for an isolated motion that does not disturb the deep sleep but prolonged movement may be considered as an indicator of restless sleep. Now, the processing circuitry may monitor the measurement signal in view of the motion threshold 312 and, simultaneously, in view of the temporal threshold 310. In an embodiment, when the measurement signal stays substantially above the motion threshold 312 for a time interval longer than the temporal threshold 310, the processing circuitry may trigger detection of the restless sleep signal pattern. Wording "substantially above the motion threshold 312" may be considered such that it is not necessary for the measurement signal to stay continuously above the motion threshold for the whole duration of the temporal threshold 310. The user's motion during the sleep is intermittent and the user may stay still for a period during the restless sleep.

In an embodiment, the processing circuitry may determine that the measurement signal stays substantially above the motion threshold 312 for a time interval longer than the temporal threshold 310 when at least a determined percentage of the time interval is spent the measurement signal staying above the motion threshold 312.

In an embodiment, the processing circuitry may determine that the measurement signal stays substantially above the motion threshold 312 for a time interval longer than the temporal threshold 310 when at least a determined number of peaks or other signal samples exceeding the motion threshold 312 is detected in the measurement during the time interval.

When examining the operation of the processing circuitry, the processing circuitry may monitor the measurement signal by comparing a level of the measurement signal with the motion threshold. When the level measurement signal exceeds the threshold (peak 300), the processing circuitry may start a timer counting the temporal threshold 310. If the measurement signal does comprise a sufficient number of samples above the motion threshold 312 within the time of the temporal threshold, as in the case of peak 300, the processing circuitry may omit triggering the detection of the restless sleep signal pattern. If the measurement signal comprises a sufficient number of samples above the motion threshold 312 within the time of the temporal threshold, as in the case of peaks 302, the processing circuitry may trigger the detection of the restless sleep signal pattern.

The temporal threshold may have the length of any one of the following: 20 seconds 30 seconds, 40 seconds, 50 seconds, 60 seconds, 70 seconds, 80 seconds, 90 seconds, two minutes, three minutes, four minutes, or five minutes. Any other value between 20 seconds and five minutes may be used as well.

Block 206 evaluates the signal components of the measurement signal that exceed the motion threshold 312. Block 208 may evaluate the signal components that are below the motion threshold 312 to estimate the continuous sleep or deep sleep. However, block 208 may employ a different threshold, e.g. a threshold that is below the motion threshold 312 used in block 206.

In block 208, the processing circuitry accumulates the time the measurement signal stays substantially below the motion threshold 312 whenever the time is longer than a temporal threshold for continuous sleep 410. The wording "stays substantially below the motion threshold" may be considered such that the processing circuitry has not detected a restless sleep signal pattern. For example, a peak 400 of the measurement signal that does not trigger the detection neither interrupts the accumulation of the continuous sleep. The processing circuitry may suspend the accumulation of the continuous sleep upon detecting the restless sleep signal pattern and resume the accumulation when the measurement signal has stayed substantially below the motion threshold for the duration of the temporal threshold 410. Continuous sleep signal patterns 400 are illustrated in FIG. 4.

In an embodiment, the temporal threshold specifies any one of the following time intervals, five minutes, six minutes, seven minutes, eight minutes, nine minutes, ten minutes, 11 minutes, 12, minutes, 13 minutes, 14 minutes, 15 minutes, and 20 minutes. Any other value between five and 20 minutes may be used as well.

Figure 5:
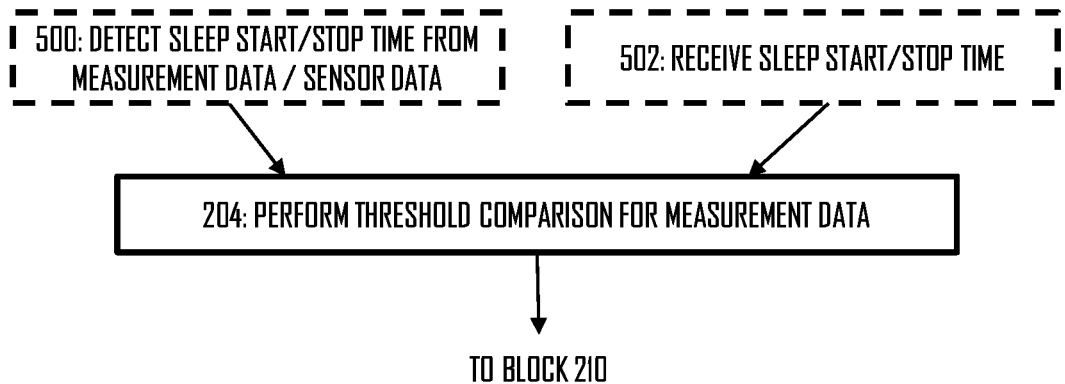
FIG. 5 illustrates a process for determining a sleep start/stop time according to an embodiment of the invention.

FIG. 5 illustrates an embodiment of block 202. In an embodiment, the processing circuitry receives the sleep start and/or stop time in block 502. The sleep start and/or stop time may be received as user input or as a result of pre-processing the measurement data, e.g. in the sensor device. For example, the sensor device may compute a hypnogram from the measurement data and output the sleep start/stop time to the processing circuitry as derived from the hypnogram. The hypnogram represents different states of the sleep, for example in the following categories: awake, REM sleep, non-REM sleep. A time instant of a transition from the awake state to the REM or non-REM sleep state may trigger the detection of the sleep start time, and a time instant of a transition from the REM or non-REM sleep state to the awake state may trigger the detection of the sleep stop time.

In another embodiment, at least the sleep start time is detected from the measurement data provided by one or more of the sensor devices (block 500). For example, the processing circuitry may detect the sleep start time when the motion sensor indicates that the user is lying still for a determined time period. The processing circuitry may employ further information such as time of the day and an estimate of the user's circadian rhythm. For example, the sleep start time may be detected only during a determined time of the day when the user 10 is assumed to go to sleep. The processing circuitry may employ a further sensor to detect the sleep start time. For example, a photo sensor may be used to detect when the user is starting to sleep. When the photo sensor indicates a low lighting condition, e.g. measured light intensity remains below a determined light intensity threshold for a determined time interval, the sleep start time may be triggered. Again, the processing circuitry may employ further information such as a combination of the photo sensor and a motion sensor. When measurement data provided by the photo sensor indicates low lighting condition and measurement data provided by the motion sensor that the use is lying still, the processing circuitry may trigger the sleep start time. Also, the time of the day and the circadian rhythm may be used as additional condition in the above-described manner.

In a similar manner, the processing circuitry may estimate the sleep stop time form the measurement data. For example, when the motion data indicates that the user has risen up, the processing circuitry may trigger the sleep stop time. Blocks 500 and 502 are mutually alternative and both of them are not necessary, as indicated in the above description.

Figure 6:
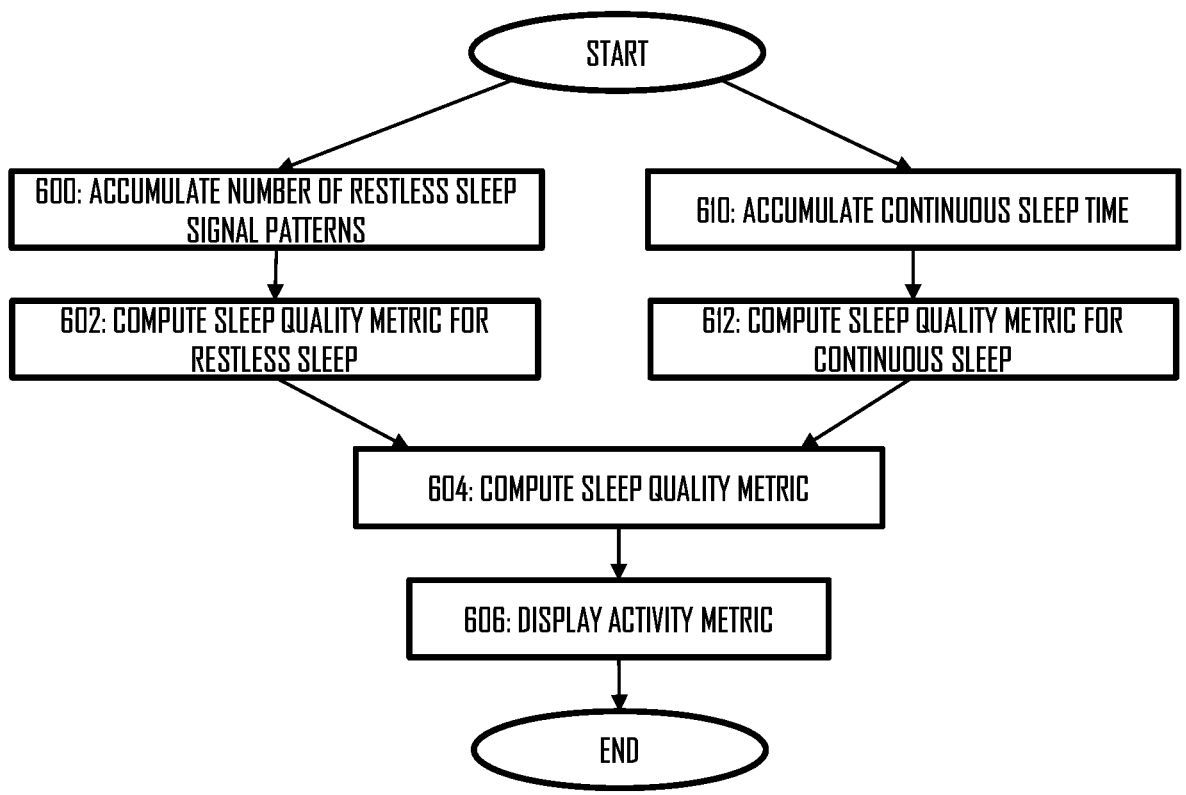
FIG. 6 illustrates an embodiment of the process of FIG. 2.

FIG. 6 illustrates an embodiment of block 210. The processing circuitry may run two parallel processes: in block 600 accumulates the number of detected restless sleep signal patterns; and in block 610 accumulates the amount of continuous sleep not interrupted by a restless sleep signal pattern within a time interval defined by the temporal threshold 410. In block 610, the processing circuitry may resume accumulation after the time interval defined by the temporal threshold 410 has passed from the latest detection of a restless sleep signal pattern.

After the sleep stop time has been detected or specified, the processing circuitry may execute block 602 where the processing circuitry computes a first sleep quality metric by using the number of accumulated restless sleep signal patterns. In an embodiment, the first sleep quality metric is computed by using the following equation:

$$SQM_1 = \frac{T - N_{int}}{T},$$

where $N_{int}$ is the number of detected restless sleep signal patterns and T is a constant, e.g. T=100, T=200, or T=50.

After the sleep stop time has been detected or specified, the processing circuitry may execute block 612 where processing circuitry computes a second sleep quality metric by using the accumulated amount of continuous sleep. In an embodiment, the second sleep quality metric is computed by using the following equation:

$$SQM_2 = \frac{T_{con}}{T_{tot}},$$

where $T_{con}$ is the accumulated amount of continuous sleep during the sleep and $T_{con}$ is the total amount of sleep. The second sleep quality metric may represent a relation between the total length of the detected one or more continuous sleep intervals and a duration from the sleep start time to the sleep stop time. The total amount of sleep may be computed from a time between the sleep start time and the sleep stop time. In other words, the second sleep quality metric indicates a portion of the total amount of sleep that the user is sleeping the continuous sleep.

In an embodiment, both the first and second sleep quality metrics are scaled between [0, 1], and an overall sleep quality metric is computed in block 604 as an average of the first and second sleep quality metric. The average may weight all sleep quality metrics equally or unequally. In some embodiments, the overall sleep quality metric is computed by using only one of the sleep quality metrics although multiple sleep quality metrics would be available. The processing circuitry may make a determination of not to use one or more of the sleep quality metrics in the computation of the overall sleep quality metric.

In another embodiment, another scale is used but both sleep quality metrics are scaled to the same scale. In block 606, the overall sleep quality metric is displayed to the user. In another embodiment, block 606 may comprise outputting the overall display metric, e.g. from the server computer to a client device over a network connection.

In an embodiment, the sleep quality metric is a value or another classification, e.g. a sleep score. The sleep quality metric output to the user may provide the user with at-a-glance type of feedback of the sleep quality. The processing circuitry may employ in the computation of the sleep quality metric the continuity of the sleep and the number of restless sleep periods in the above-described manner and, additionally, employ at least some of the following data: total sleep time, amount of REM sleep, amount of non-REM sleep, a number of sleep cycles, amount of time spent on each sleep state, estimated depth of sleep, and other measurement data provided by the at least one sensor device. During normal sleep, a person experiences different sleep states in a cyclic manner, and the number of sleep cycles has been discovered to correlate with the sleep quality. A time spent on the sleep states inherently correlates with the sleep quality. For example, a long time spent in the awake state results in poor sleep quality, while a high sleep quality may be achieved by spending some time in a REM sleep state and some time in a non-REM sleep state or a deep sleep state. In an embodiment, the sleep score may be computed by using a function of a weighted sum of total time spent in each sleep state between the sleep start time and the sleep stop time. In another embodiment, the sleep score may be computed by comparing the time spent on each sleep state with a target time to be spent on each sleep state, and aggregated the comparison results achieved for the different sleep states. A higher score for a sleep state may be achieved when the time spent on the sleep state is closer to the target, while a lower score for a sleep state may be achieved when the time spent on the sleep state is further away from the target. The aggregation may include a (weighted) sum of the sleep scores for the different sleep states. The depth of sleep may be estimated from the hypnogram, for example, or from the time spent on each sleep state. The longer the user spends on the deep sleep state, the deeper is the depth of sleep. The other measurement data may include, for example, heart rate variability (HRV) measurement data. The HRV is a physiological phenomenon of variation in a time interval between consecutive heartbeats. The HRV is measured by the variation in the beat-to-beat interval at a substantially constant heart rate. Other terms used instead of the HRV are cycle length variability and RR-variability.

Figure 15:
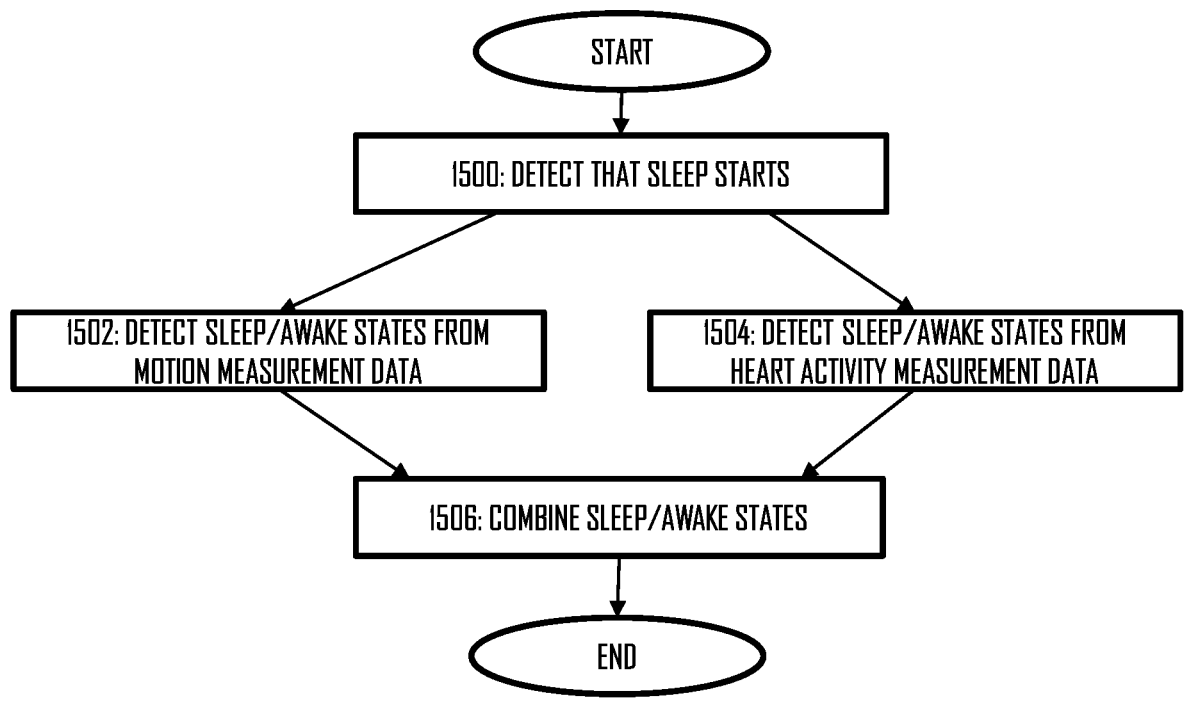
FIG. 15 illustrates a process for estimating sleep states by using motion measurement data and heart activity measurement data according to an embodiment of the invention.

As described above, both heart activity measurement data and motion measurement data may be used in the estimation of the sleep quality. In an embodiment the heart activity measurement data and the motion measurement data are both measured during sleep and combined into the sleep quality according to a determined scheme. In an embodiment, a first sequence of sleep states or, equivalently, sleep stages during the sleep are estimated from the heart activity measurement data, and a second sequence of sleep states during the sleep are estimated from the motion measurement data. The two sequences of sleep states are then combined into a single sequence of sleep states between the sleep start time and the sleep stop time. FIG. 15 illustrates such an embodiment. Referring to FIG. 15, the sleep start time is detected in block 1500, e.g. from the motion measurement data. This may trigger execution of blocks 1502 and 1504.

In block 1502, sleep states are detected from the motion measurement data. The motion measurement data, e.g. acceleration data, may be used to estimate whether the user is in the awake state or in one of the sleep states associated with sleeping, e.g. REM sleep state or a non-REM sleep state. In some embodiments, the particular sleep state associated with sleeping is not detected from the motion measurement data.

Figure 17:
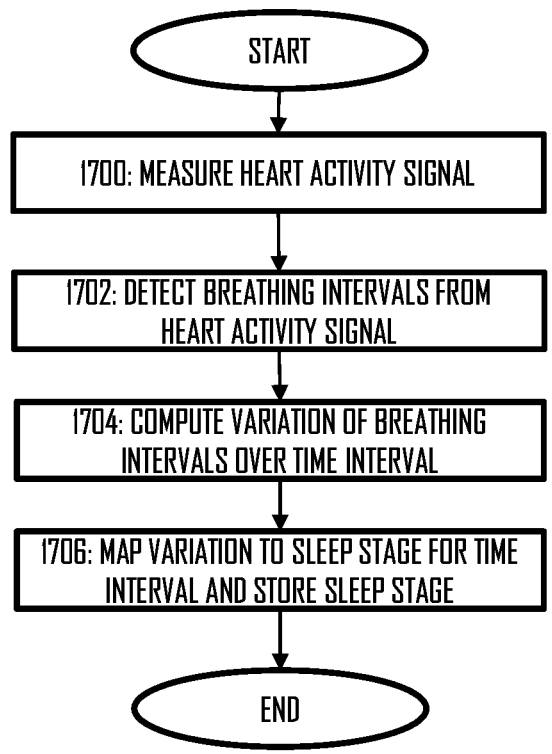
FIG. 17 illustrates an embodiment for detecting sleep states from heart activity measurement data.

In block 1504, sleep states are detected from the heart activity measurement data, e.g. PPG, ECG, or BCG measurement data. The heart activity measurement data may indicate the sleep states in the HRV, for example. FIG. 17 described below illustrates an embodiment where respiratory rate or breathing frequency is estimated from the heart activity measurement data. The breathing frequency may then be used as an indicator of the sleep state. The heart activity measurement data may be used to determine the sleep states with higher resolution than what the motion measurement data indicates. The heart activity measurement data may indicate the sleep state within the sleep states associated with sleeping. In an embodiment, the heart activity measurement data is not used for determining that the user is awake. Only motion measurement data may be used when determining whether the user is awake or sleeping in this embodiment.

Blocks 1502 and 1504 provide a sequence of sleep states estimated between the sleep start time and the sleep stop time. In block 1506, the sequences of sleep states are combined. The combining may be made between sleep states associated with the same timing and, for that purpose, time reference may be stored in connection with the sleep states detected in blocks 1502 and 1504.

In the following embodiment describing the combining, four sleep states are used: awake, REM sleep, light non-REM sleep, and deep non-REM sleep. In other embodiments, a different number of sleep states may be used while maintaining the combining principles.

In an embodiment of block 1506, Table 1 may be applied when combining a sleep state determined from the motion measurement data with a sleep state determined from the heart activity measurement data:

TABLE 1

| Sleep state (motion) | Sleep state (heart activity) | Combined sleep state |
| --- | --- | --- |
| Awake | — | Awake |
| Awake | REM sleep | Awake |
| Awake | Light non-REM sleep | Awake |
| Awake | Deep non-REM sleep | Awake |
| Sleep | REM sleep | REM sleep |
| Sleep | Light non-REM sleep | Light non-REM sleep |
| Sleep | Deep non-REM sleep | Deep non-REM sleep |

The following general rules may be drawn from the rules of Table 1:
1) If the motion measurement data indicates that the user is awake, the combined sleep state is awake, even if the heart activity measurement data indicates that the user is sleeping;
2) If the motion measurement data indicates that the user is sleeping, the heart activity measurement data is used to determine the sleep state within those states associated with the sleeping, e.g. REM sleep, light non-REM sleep, and deep non-REM sleep.

Figure 16:
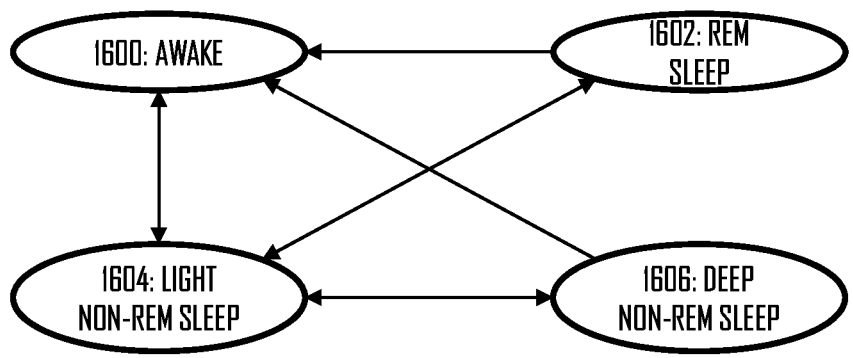
FIG. 16 illustrates a sleep state transition diagram used in some embodiments of the invention.

Further constraints may be used in the combining, as described now in connection with a state diagram of FIG. 16. It has been discovered that the sleep states follow a certain pattern within the constraints illustrated in FIG. 16. FIG. 16 illustrates the above-described sleep states, i.e. awake 1600, REM sleep 1602, light non-REM sleep 1604, and deep non-REM sleep 1606. Certain rules may be provided according to which the state transitions occur in the sleep, and the combining in block 1506 may be constrained by these rules. For example, scientists have discovered that a human transitions from the deep non-REM sleep 1606 to the REM sleep 1602 only through the light non-rem sleep state 1604 or through the awake state 1600. Similarly, the deep non-REM sleep state 1606 may only be reached via the light non-REM sleep state 1604. Further, the REM sleep 1602 may be entered only via the light non-REM sleep.

Therefore, in an embodiment of block 1506, the combining is further constrained by at least some of the constraints described above. For example, if the combining in block 1506 results in a state transition to the REM sleep state 1602, the procedure may then check a directly previous sleep state. If the previous sleep state is the light non-REM sleep 1604, the procedure may allow the state transition to the REM sleep state 1602. However, if the previous sleep state is either the awake state 1600 or the deep non-REM sleep state 1606, the procedure may carry out state transition to the light non-REM sleep state 1604. If the next combining operation(s) result(s) indicate maintained REM sleep state 1602, the procedure may then carry out the state transition to the REM sleep state 1602. In an embodiment, the light non-REM sleep state 1604 is maintained for a determined duration before the transition to the REM sleep state 1602 is allowed. The determined duration may be measured by using a timer triggered upon state transition from the state 1600 or 1606 to the state 1604 in a situation where the combining result indicates the state 1602. A condition may be that the combining in block 1506 shall indicate the state 1602 for the whole duration the timer is counting or, in another embodiment, a majority of the duration the timer is counting.

If the combining in block 1506 results in a state transition to the deep non-REM sleep state 1606, the procedure may then check a directly previous sleep state. If the previous sleep state is the light non-REM sleep 1604, the procedure may allow the state transition to the deep non-REM sleep state 1606. However, if the previous sleep state is either the awake state 1600 or the REM sleep state 1602, the procedure may carry out state transition to the light non-REM sleep state 1604. If the next combining operation(s) result(s) indicate maintained deep non-REM sleep state 1606, the procedure may then carry out the state transition from the state 1604 to the deep non-REM sleep state 1606. In an embodiment, the light non-REM sleep state 1604 is maintained for a determined duration before the transition to the deep non-REM sleep state 1606 is allowed. The determined duration may be measured by using a timer triggered upon state transition from the state 1600 or 1602 to the state 1604 in a situation where the combining result indicates the state 1606. A condition may be that the combining in block 1506 shall indicate the state 1606 for the whole duration the timer is counting or, in another embodiment, a majority of the duration the timer is counting.

Figure 18:
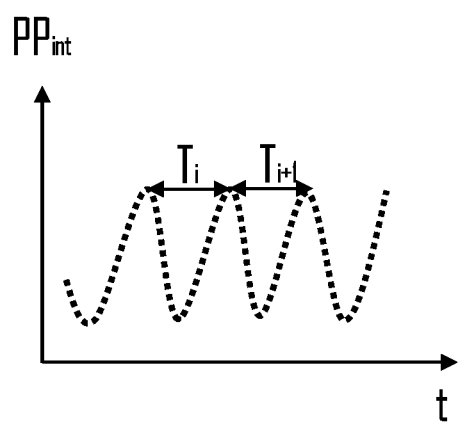
FIG. 18 illustrates a peak-to-peak interval graph for a heart activity signal.

Let us now describe some embodiments of block 1704 with reference to FIG. 17. Referring to FIG. 17, the breathing intervals are detected from a measured heart activity signal, e.g. a PPG signal. In block 1700, the PPG signal is measured from the user. In block 1702, the heart activity signal is processed and breathing intervals are detected from the heart activity signal. The breathing intervals can be detected from a set of peak-to-peak interval values of the measured PPG signal. FIG. 18 illustrates a set of these peak-to-peak interval values $PP_{int}$ of a PPG signal. The peak-to-peak interval values fluctuate according to the breathing and form a set of samples $PP_{int}$ having a sinusoidal form. Peak-to-peak intervals $T_i$, $T_{1+1}$, . . . of the peak-to-peak interval values $PP_{int}$ correlate with the breathing frequency. Frequency of the signal formed by the peak-to-peak interval values $PP_{int}$ corresponds to the breathing frequency and, therefore, a Fourier transform of the peak-to-peak interval values $PP_{int}$ has been conventionally used to estimate the breathing frequency.

In an embodiment, instead of computing the breathing frequency, the breathing intervals are used. The breathing intervals may be computed in a time domain from the PPG signal. In a similar manner, the breathing intervals may be computed from heart activity measurement data acquired by using another sensor, e.g. ECG or BCG sensor. The breathing intervals may be computed from variation of RR intervals of an ECG signal. The breathing frequency also derivable from a phase component of the ECG signal. Upon acquiring the breathing interval samples $T_s$, where $s \in [0, S]$, some averaging may be performed for the samples over an averaging window. This smoothing may, however, be optional.

In block 1704, the variation of the breathing intervals $T_s$ are computed. In an embodiment, the variation of breathing intervals $T_s$ is computed as a standard deviation of a set of measured breathing interval samples. The set may be associated with a determined time interval, e.g. 50, 60, or 70 seconds. The time interval may define the temporal resolution for the sequence of sleep states. For example, if the time interval is 60 seconds, the sleep states is evaluated every minute. In another embodiment, the temporal resolution needs not to be bound to the time interval. For example, a rolling value for the breathing intervals may be computed with a determined periodicity by using the samples acquired within the determined time interval, wherein the period is shorter than the time interval. The period may be 30 seconds, and the time interval may be 60 seconds, for example.

The computed variation, e.g. the standard deviation, may then be mapped to one of the sleep state according to a mapping table that maps the variation values to the sleep states (block 1706), and the sleep state may then be stored for further processing and output to the user interface. In an embodiment, the variation is scaled to a determined range, wherein the scaling may use as a reference variation of the breathing frequency computed within a time window. This time window may be longer than the time interval used for determining the variation, e.g. the standard deviation. In an embodiment, the time window is several hours, e.g. two, three or four hours. In another embodiment, the time window is the past time from the sleep start time. A minimum value of the variation and a maximum value of the variation within the time window may be determined for the scaling. The minimum value may set the lowest value of the range, and the maximum value may set the highest value of the range. In an embodiment, the range is [0, 1], and the variation is mapped to this scale depending on the variation with respect to the minimum and maximum values. The sleep states may be defined within the range according to a determined criterion, e.g. as illustrated in Table 2 below. For example, the awake state may be associated with the maximum value of the range, while the deep non-REM sleep state may be associated with the minimum value of the range. Boundaries of the remaining states may then be set accordingly between sub-ranges of the awake state and the deep non-REM sleep state.

TABLE 2

| Sleep state | Scaled Range |
| --- | --- |
| Deep non-REM sleep | 0 to X1 |
| Light non-REM sleep | X1 to X2 |
| REM sleep | X2 to X3 |
| Awake | X3 to 1 |

In another embodiment, the breathing interval samples $T_s$ are acquired from an acoustic sensor. In such an embodiment, block 1504 may be modified such that the sleep and awake states are determined from the acoustic measurement data.

Figure 7:
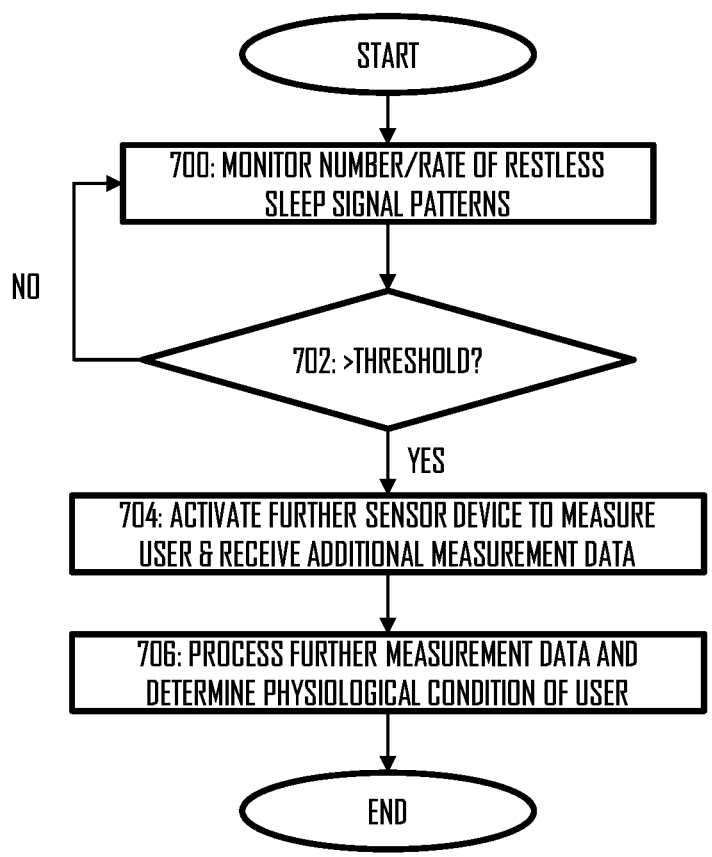
FIG. 7 illustrates a process for detecting unusual sleeping behaviour and triggering an action according to an embodiment of the invention.

In an embodiment, the method of FIG. 2 is used to detect unusual sleeping behaviour. FIG. 7 illustrates a process for detecting the unusual sleeping behaviour and triggering further measurements on the user. The process of FIG. 7 may be carried out by the processing circuitry. Referring to FIG. 7, the process comprises monitoring the number or rate of the restless sleep signal patterns (block 700) and comparing the number or rate of the restless sleep signal patterns with a threshold (block 702). If the number or rate of the restless sleep signal patterns exceeds the threshold, the process may proceed to block 704 where the processing circuitry activates a further sensor device to measure the user and provide the processing circuitry with further measurement data.

In an embodiment, the measurement data used in block 700 is motion measurement data, and the processing circuitry activates a heart activity sensor in block 704. The heart activity sensor may measure the ECG, PPG, or BCG of the user. In another embodiment, the processing circuitry activates an EEG sensor in block 704. In another embodiment, the processing circuitry activates a bioimpedance or galvanic skin response sensor in block 704. In another embodiment, the processing circuitry activates a respiratory rate sensor in block 704. In block 706, the processing circuitry processes the further measurement data and determines a physiological condition of the user 10. For example, the processing circuitry may attempt to detect one or more indicators of a physiological disorder or disease from the further measurement data. The determined physiological condition may be output in block 210.

In another embodiment, instead of activating a sensor device in block 704, the processing circuitry may output a notification to the user. The notification may comprise information of detected unusual sleeping behaviour and a suggestion to perform a test, e.g. an orthostatic test. The processing circuitry may also propose a schedule for the test by using user's calendar such that the proposed schedule does not cause a conflict with another event in the user's calendar.

In another embodiment, the processing circuitry monitors another feature in block 700. The factors that may indicate the unusual sleeping behaviour may include prolonged duration in falling asleep, changes in physical activity during sleep, changes in a rhythm of sleep-states such as REM and non-REM states, and changes in overall sleep duration. The processing circuitry may use further information in block 700 such as user's activity while the user 10 is awake. For example, if the user has performed a demanding exercise just before the sleep, the processing circuitry may consider that the sleep quality is degraded because of the exercise and not trigger the execution of block 704. In a similar manner, if the user has increased a training load of physical exercises, the processing circuitry may consider that the sleep quality is degraded because of the training load and not trigger the execution of block 704.

As yet another example of the further information used in block 700, the processing circuitry may employ location data. Many personal electronic devices track the user's location by using sensors or networking. If the location of the user 10 is not mapped to the user's home, the processing circuitry may consider that the user may sleep worse outside home and not trigger the execution of block 704 in a situation where block 704 would be triggered when the location of the user is mapped to the home.

In the above-described embodiments of FIG. 7, the processing circuitry may skip the process of FIG. 7 unless certain conditions defined by the additional information are fulfilled, e.g. the conditions are normal in a sense that the user should be sleeping well.

Figure 8:
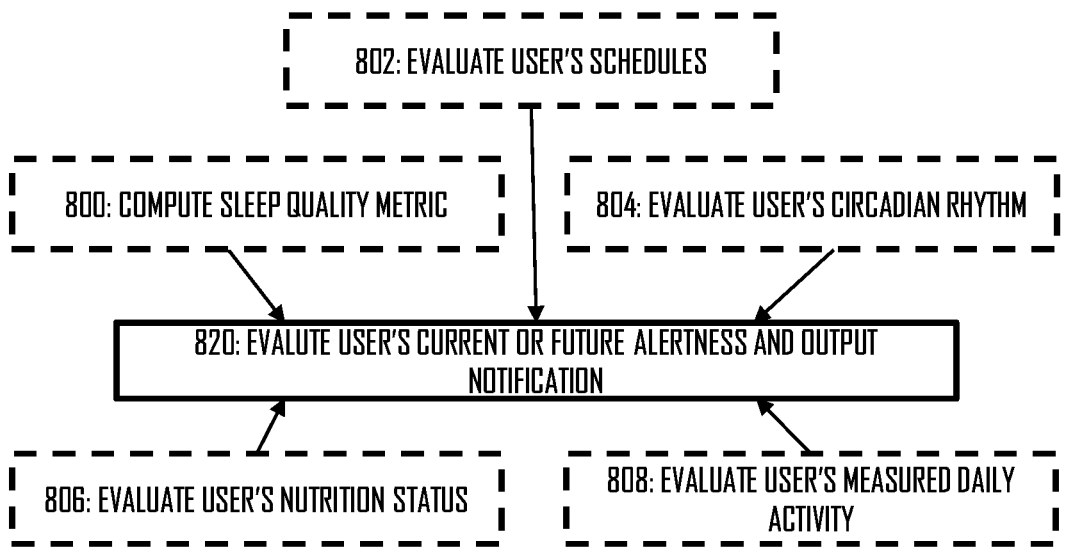
FIG. 8 illustrates a process for estimating an alertness level of a user according to an embodiment of the invention.

In an embodiment, the process of FIG. 2 is used in estimation of an alertness level of the user 10. FIG. 8 illustrates an embodiment of a process for estimating the current or future alertness level in a computer process executed by the processing circuitry. In the embodiment of FIG. 8, the processing circuitry employs multiple inputs in the estimation of the user's current alertness level or in prediction of the user's alertness level in the future, e.g. the next day when the user has scheduled a competition. In the future prediction, the processing circuitry may first determine a future time instant to which the prediction is targeted and then estimate the future alertness on the basis of the information on the user currently available to the processing circuitry.

Referring to FIG. 8, the processing circuitry estimates the alertness level in block 820 and outputs the estimated alertness in the form of a notification. The processing circuitry may classify the alertness according to a classification scheme comprising multiple alertness classes and map the estimated alertness level to one of the classes. The different types of information on the user available may affect the estimated alertness level in a degrading or improving manner, as described below.

The processing circuitry may use the sleep quality metric computed in block 800 according to any one of the above-described embodiments in block 820. The processing circuitry may employ a database mapping different values of the sleep quality metric to different alertness levels and determine an alertness level associated with the sleep quality metric received as a result of block 800. A sleep quality metric associated with longer continuous sleep and less interrupted sleep may map to a higher alertness level class in the database.

The processing circuitry may use in block 820 user's circadian rhythm and current time of the day, as determined in block 804. If the user's circadian rhythm indicates that the user should currently be asleep while the measurement data indicates that the user is not sleeping, the processing circuitry may map this information to a lowered alertness level. On the other hand, if the user's circadian rhythm and the measurement data indicates that the user has slept, the input from block 804 may cause determination of a high alertness level. Circadian rhythm may be used by the processing circuitry when mapping the sleep quality metric(s) to the alertness level. For example, if the user has slept well as indicated by the sleep quality metric(s) and during natural sleeping hours as indicated by the circadian rhythm, the processing circuitry may output a value indicating a higher alertness level. On the other hand, if the if the user has slept well as indicated by the sleep quality metric(s) but outside natural sleeping hours indicated by the circadian rhythm, e.g. during the daylight and less or not at all during the night, the processing circuitry may output a value indicating a lower alertness level. If the user has not slept well as indicated by the sleep quality metric(s) and mainly outside the natural sleeping hours indicated by the circadian rhythm, the processing circuitry may output a value indicating an even lower alertness level.

The processing circuitry may use measurement data provided by a thermometer measuring the user's temperature. Temperature measurement may improve the estimate of the circadian rhythm and accuracy of the alertness estimate. It has been discovered that bodily temperature can be used as a measure of the user's circadian rhythm because the temperature evolves in the same (24 hour) cycles as the circadian rhythm. The processing circuitry may utilize this information in the estimation of the circadian rhythm on the basis of temperature measurement data measured from the user.

The processing circuitry may adapt the user's circadian rhythm on the basis of the measurement data and/or on the basis of user' electronic calendar events. For example, if the location of the user is mapped to a new time zone indicating that the user has traveled, the processing circuitry may adapt the circadian rhythm to the new time zone. Instead of the location mapping performed on the basis of measurement data received from a satellite positioning receiver such as a GPS (Global Positioning System) receiver, the processing system may detect the travelling from the contents of the calendar events and adapt the circadian rhythm to the new time zone on the basis of the calendar data.

The processing circuitry may use in block 820 the user's nutrition status evaluated in block 806. The user may input nutrition intake through a user interface, e.g. in terms of calories or another energy intake metric or as type and an amount of nutrition intake. The processing circuitry may compute in block 806 or receive as a result of block 806 the user's current nutrition status and take the nutrition status into account in the estimation of the alertness level. The processing circuitry may take the nutrition status into account according to a function or database that maps the effect of the nutrition status to the alertness level. A low nutrition status indicates a lower alertness level and a high nutrition status indicates a higher alertness level, when considering other factors as constant.

The processing circuitry may use in block 820 any measurement data that represents the user physical activity earlier, e.g. on the same day and/or previous day(s). Block 808 may comprise evaluating the physical activity the user has performed, e.g. a training load estimate or an energy expenditure value and outputting the result of the evaluation to block 820. The processing circuitry may then map an effect of the physical activity to the alertness evaluation. For example, a high training load caused by one or more demanding physical exercise may affect the alertness level in a degrading manner. On the other hand, very low physical activity may also affect the alertness level under some circumstances. Moderate physical activity may affect the alertness level in an improving manner, in particular during the next few hours following the activity.

Regarding the estimation of the future alertness, the processing system may search the user's calendar or another schedule for a future event such as a sporting event (block 802). The processing system may then estimate the user's alertness at the future event by using the information available from any one or more of the blocks 800, 804 to 808. For example, if the sleep quality metric received from block 800 indicates poor sleep quality, the processing system may degrade an estimate of the alertness level in the future event. The processing system may output a notification suggesting the user to go to sleep in order to be alert in the event.

In an embodiment, the processing circuitry may compute an alertness value representing the alertness level for each piece of information available from one or more of the blocks 800 to 808. For example, the processing circuitry may map the sleep quality metric received from block 800 to a first alertness value, nutrition status received from block 806 to a second alertness values, measured activity received from block 808 to a third alertness value, and so on. Thereafter, the processing circuitry may combine the alertness values into an aggregate alertness values and output the aggregate alertness value or a notification derived from the aggregate alertness values. The combining may be performed by averaging or weighted averaging of the first, second, third, etc. alertness values.

In an embodiment, the processing circuitry determines that the alertness metric or the future alertness metric crosses a threshold level indicating a threshold alertness level and, in response to said determining, the processing circuitry outputs a notification of degrading alertness level to the user. For example, when the user is detecting performing an action requiring an alertness level above the threshold level, a drop in the estimated alertness level below the threshold level may trigger output of an alarm to the user.

Regarding the notification, the notification may indicate the current or future alertness, as described above, and/or it may include smart guidance to the user. The guidance may instruct the user to do actions that improve the alertness, e.g. recommend a sleep time or sleep duration, take a physical exercise, improve nutrition intake, take a test such as the orthostatic test or a psychomotor vigilance task (PVT) test. The PVT test may be used to calibrate the alertness estimation in block 820. The PVT test may indicate the user's current real alertness level, and the processing system may calibrate its current estimate of the alertness level to a level indicated by the PVT, if they differ.

Figure 9:
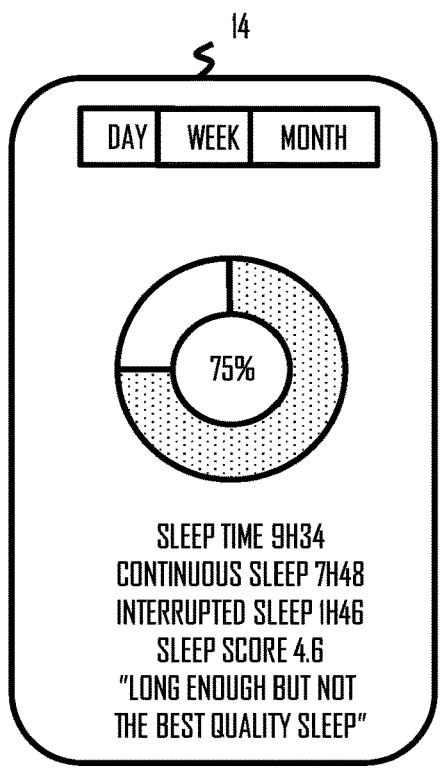
FIGS. 9 to 12 illustrate display views according to some embodiments of the invention.

FIGS. 9 to 12 illustrate examples of display outputs indicating the sleep quality estimated according to any one of the above-described embodiments. FIG. 9 illustrates a display view indicating the amount of continuous sleep as accumulated in block 610, an amount of interrupted sleep, a percentage of continuous sleep (75% in this example), a sleep score as computed in block 604, for example, and verbal feedback of sleep quality. The verbal feedback may comprise an instruction as how to improve the sleep quality.

Figure 10:
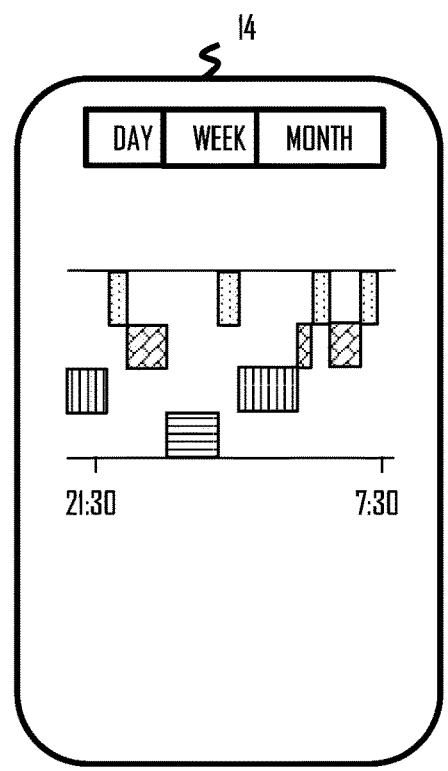

FIG. 10 illustrates a display view where the sleep over one night is illustrated as divided into different sleep stages within the night. The display view may illustrate the sleep start time (21:30) and the sleep stop time (7:30), as determined in the above-described manner. The display view may also illustrate how the sleep has evolved between the sleep stages over the night. This example employs four sleep stages illustrated by different patterns but the number of different stages may be different.

Figure 11:
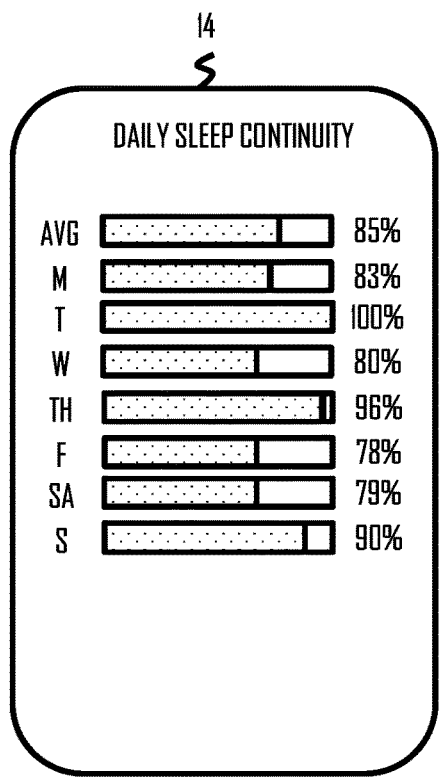

FIG. 11 illustrates a weekly display view where the continuous sleep and interrupted sleep are illustrated on a daily basis and, additionally, a weekly average is displayed. The amount of continuous sleep versus the amount of interrupted sleep may be illustrated for each day. In any one of the display views, the number of restless sleep intervals as accumulated in block 600 may be displayed.

Figure 12:
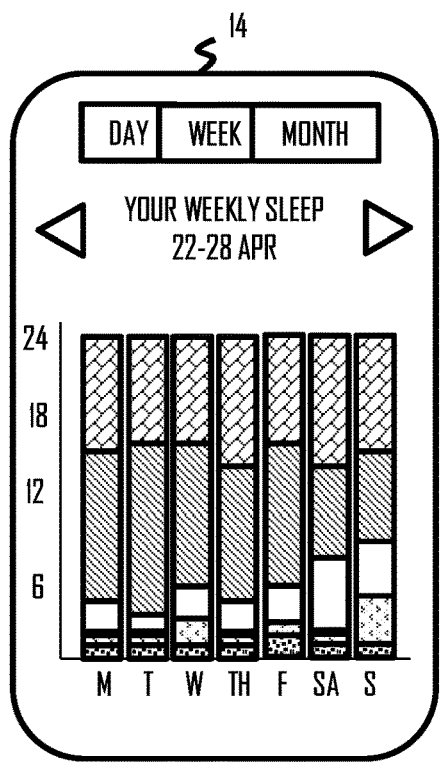

FIG. 12 illustrates a display view which is a weekly display view of FIG. 10. Accordingly, the display view of FIG. 12 may illustrate for each day of the week an amount of time spent on each of the sleep stages. As described above, the number of sleep stages may depend on the implementation of the sleep analysis.

In modern smart computing systems and portable electronic devices, a dedicated computer program of an electronic device may compute the sleep quality metric ort monitor the sleep quality according to any one of the above-described embodiments. However, the results of the sleep quality analysis may be used other computer program applications of the electronic device. The computer programs may exchange the information on the sleep quality through an application programming interface (API) of the electronic device. As known by the person skilled in the computer programming, an API is a set of clearly defined methods of communication between different computer programs. The communication may allow one computer program to retrieve certain information from another computer program according to a determined protocol defined by the API.

Figure 13:
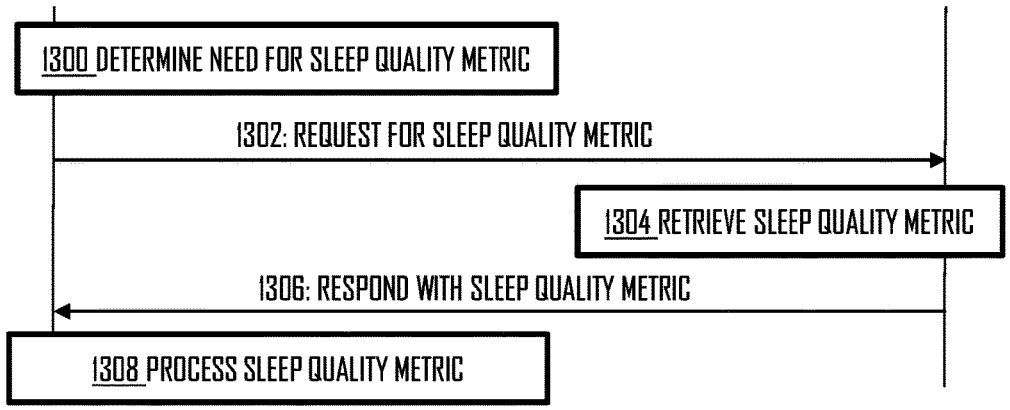
FIG. 13 illustrates a process for communicating over an application programming interface according to an embodiment of the invention.

FIG. 13 illustrates an embodiment for communicating over an API within the electronic device. Referring to FIG. 13, a computer program application such as a lifestyle application or a gaming application may require the sleep quality metric according to any one of the above-described embodiments as an input. The computer program application may be aware that the sleep quality metric is available, as provided by a sleep quality evaluation application also executed in the electronic device. In block 1300, the computer program application determines a need for the sleep quality metric. As a response, the computer program application formulates a request for sleep quality metric and sends the request over the API to the sleep quality evaluation application (step 1302). The request may be in a form "GET URL" where URL specifies a resource storing the sleep quality metric. Upon receiving the request in step 1302, the sleep quality evaluation application may process the request, retrieve the requested information (the sleep quality metric in block 1304), and formulate a response to the request. The response may carry the requested sleep quality metric, and the sleep quality evaluation application may send the response over the API in step 1306. Upon receiving the response and the sleep quality metric, the computer program application may employ the sleep quality metric in its execution.

The sleep quality metric may be the sleep score or the amount of continuous sleep, for example.

FIG. 13 illustrates a request-response process for retrieving the sleep quality metric over the API on-a-demand basis. In another embodiment, the sleep quality evaluation application may report the sleep quality metric over the API periodically, e.g. daily.

Instead of an internal API between computer programs executed in the electronic device, e.g. an API of Android Wear® operating system, the interface may be a Bluetooth® or another radio interface and the communication illustrated in FIG. 13 may be carried out over a radio interface by exchanging radio frames in steps 1302 and 1306.

An embodiment comprises a data structure for an application programming interface (API) in a computer system, comprising: a header comprising control information specific to the API; and a data portion comprising the sleep quality metric according to any one of the above-described embodiments. In an embodiment, the data structure may have the following format:

| Header | Payload Data | CRC |
|--------|--------------|-----|

The header may comprise control or management information needed to deliver the payload data, the payload data may comprise the sleep quality metric, the alertness value, or any other piece of information computed by the processing circuitry according to any one of the above-described embodiments. A cyclic redundancy check (CRC) part may comprise CRC bits for error detection and/or correction.

In an embodiment the header may have the following format:

| Pad | Preamble | Sync | Tx index | Type | Len | SensorID | Timestamp |
|-----|----------|------|----------|------|-----|----------|-----------|

Pad field may comprise padding bits that have no specific use, preamble and synchronization sequence (Sync) may comprise bits needed for detecting the data structure in a receiver and to synchronize to the header. A transmission index (Tx index) may indicate a position of the payload data in a series of data packets, and it may be used for reordering data packets and finding lost data packets. Reason field indicates a type of the data structure. The Type field or another field of the header may comprise a value indicating what type of payload data the data portion carries. One value may be reserved for the sleep quality metric to indicate that the payload data carries the sleep quality metric. One value may be reserved for the alertness level to indicate that the payload data carries the alertness level. Length field (Len) specifies the total length of the data structure, SensorID field carries an identifier of an entity that provides the data, e.g. the sleep quality evaluation application in the embodiment of FIG. 13, and Timestamp field is used for a timestamp indicating the timing of the data comprised in the payload part of the data structure.

In an embodiment, the data structure is a frame such as a radio frame. In an embodiment, the data structure is a data structure used in an operating system suitable for wearable devices, e.g. Android Wear®. In an embodiment, the data structure is a packet of a network communication protocol such as an internet protocol (IP).

Figure 14:
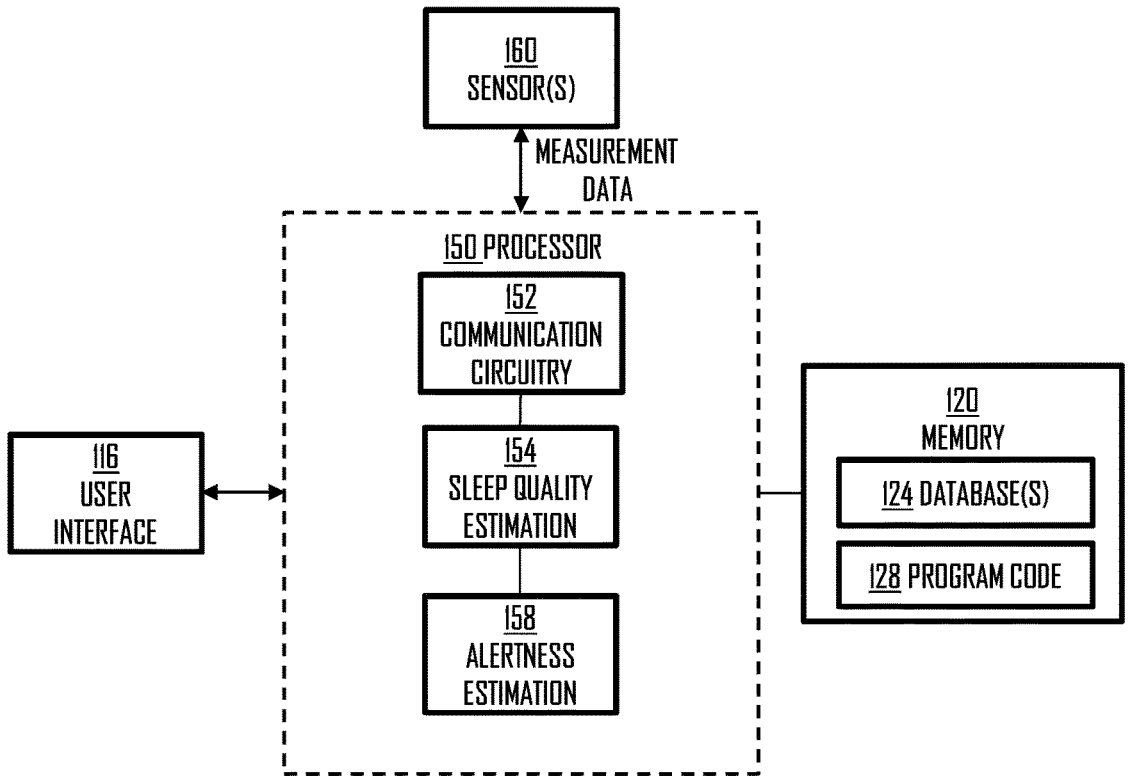
FIG. 14 illustrates a block diagram of an apparatus according to an embodiment of the invention.

FIG. 14 illustrates a block diagram of a structure of an apparatus according to an embodiment of the invention. The apparatus may be applicable to or comprised in the portable electronic device 14. In other embodiments, the apparatus is applicable to or comprised in a sensor device, a wearable device, or a server computer. The apparatus may comprise at least one processor 150 or processing circuitry and at least one memory 120 including a computer program code 128, wherein the at least one memory and the computer program code are configured, with the at least one processor, to cause the apparatus to carry out the functions described above in connection with the processing circuitry. The processor 150 may comprise a communication circuitry 152 as a sub-circuitry configured to handle wireless connection with one or more sensor devices 160 or internal connection between computer program modules through one or more APIs in the apparatus. The sensor device(s) 160 may be comprised in the apparatus, be external to the apparatus, or comprise both internal and external sensor devices. The sensor device(s) 160 may comprise at least one of the following sensors: a heart activity sensor measuring the ECG, BCG, or PPG, a motion sensor or an inertial sensor measuring motion, an EEG sensor measuring the EEG, an EOG sensor measuring the EOG, a bioimpedance sensor measuring the bioimpedance or another galvanic property from a skin, and a respiratory rate sensor measuring the respiratory rate. The communication circuitry 152 may be configured to receive measurement data from the sensor device(s). The communication circuitry may be configured to output sleep quality metrics and/or other information through an API, as described above.

The processor may comprise a sleep quality estimation module 154 configured to compute the sleep quality metrics according to any one of the embodiments of FIGS. 2 to 7. The sleep quality estimation module 154 may be configured by the computer program code 128 to map the detected restless and continuous sleep signal patterns to the sleep quality metric. The memory may store a database 124 that provides rules for the mapping of the detected signal patterns to a sleep quality classification or a sleep score, for example. When executing the embodiment of FIG. 7, the sleep quality estimation circuitry 154 may in block 704 output a notification to the communication circuitry, and the notification may cause the communication circuitry to activate one or more of the sensor device(s) 160. When executing the processes according to any one of the above-described embodiments, the sleep quality estimation module 154 may output the sleep quality metric to the user 10 via a user interface 116 comprised in the apparatus or being external to the apparatus. The user interface 116 may comprise a display screen or a display module for displaying the sleep quality metric. The user interface 116 may also comprise an input device for inputting information such as the nutrition intake.

The processor 150 may comprise an alertness estimation module 158 configured to estimate the current or future alertness level according to any one of the embodiments described above in connection with FIG. 8. The alertness estimation module 158 may employ the database in mapping the various information available to the user's alertness level. The alertness estimation module 158 may output the estimated alertness level to the user interface 116. The alertness estimation module 158 may derive one or more instructions based on the estimated alertness level, such as an instruction for the user to rest, and output the one or more instructions to the user interface 116. In an embodiment, the alertness estimation module 158 receives from the user or from the user's schedule a future time instant when the user is desired to have a target alertness level. The alertness estimation module 158 may then predict the user's alertness at the time instant on the basis of the information currently available. If the prediction indicates that the user cannot reach the target alertness level, the alertness estimation module 158 may determine corrective measures that are needed from the user to reach the target alertness level, e.g. to rest, to perform a restorative exercise, and/or to improve the nutrition intake.

As used in this application, the term 'circuitry' refers to all of the following: (a) hardware-only circuit implementations such as implementations in only analog and/or digital circuitry; (b) combinations of circuits and software and/or firmware, such as (as applicable): (i) a combination of processor(s) or processor cores; or (ii) portions of processor(s)/software including digital signal processor(s), software, and at least one memory that work together to cause an apparatus to perform specific functions; and (c) circuits, such as a microprocessor(s) or a portion of a microprocessor(s), that require software or firmware for operation, even if the software or firmware is not physically present.

This definition of 'circuitry' applies to all uses of this term in this application. As a further example, as used in this application, the term "circuitry" would also cover an implementation of merely a processor (or multiple processors) or portion of a processor, e.g. one core of a multi-core processor, and its (or their) accompanying software and/or firmware. The term "circuitry" would also cover, for example and if applicable to the particular element, a baseband integrated circuit, an application-specific integrated circuit (ASIC), and/or a field-programmable grid array (FPGA) circuit for the apparatus according to an embodiment of the invention.

The processes or methods described in FIGS. 2 to 8 may also be carried out in the form of a computer process defined by a computer program. The computer program may be in source code form, object code form, or in some intermediate form, and it may be stored in some sort of carrier, which may be any entity or device capable of carrying the program. Such carriers include transitory and/or non-transitory computer media, e.g. a record medium, computer memory, read-only memory, electrical carrier signal, telecommunications signal, and software distribution package. Depending on the processing power needed, the computer program may be executed in a single electronic digital processing unit or it may be distributed amongst a number of processing units.

The present invention is applicable to the systems described above. Such development may require extra changes to the described embodiments. Therefore, all words and expressions should be interpreted broadly and they are intended to illustrate, not to restrict, the embodiment. It will be obvious to a person skilled in the art that, as technology advances, the inventive concept can be implemented in various ways. The invention and its embodiments are not limited to the examples described above but may vary within the scope of the claims.

What is claimed is:

1. A computer-implemented method for estimating sleep quality of a user, comprising:
   receiving, by an apparatus, measurement data measured by at least one sensor device during a time interval;
   determining a sleep start time and a sleep stop time in the measurement data;
   detecting, by the apparatus from a subset of the measurement data, the subset measured between the sleep start time and the sleep stop time, one or more restless sleep signal patterns indicating a restless sleep interval longer than a first threshold duration and computing a number of the detected one or more restless sleep signal patterns;
   detecting, by the apparatus from the subset of the measurement data, one or more continuous sleep intervals not including any one of the one or more restless sleep signal patterns within a time interval longer than a second threshold duration and computing a total length of the one or more continuous sleep intervals;
   computing a relation ratio of the total length of the detected one or more continuous sleep intervals to a duration from a sleep start time to a sleep stop time;
   computing, by the apparatus on a basis of the computed relation ratio and the number of the detected one or more restless sleep signal patterns, a sleep quality metric indicating a quality of the user's sleep between the sleep start time and sleep stop time; and
   outputting, by the apparatus, the sleep quality metric.

2. The method of claim 1, wherein the second threshold duration is longer than the first threshold duration.

3. The method of claim 1, wherein a restless sleep signal pattern is detected by analysing the measurement data and detecting a signal pattern indicating user activity above a determined activity threshold for a time period longer than the first threshold duration.

4. The method of claim 3, wherein the measurement data comprises motion measurement data and the activity threshold is a motion activity threshold.

5. The method of claim 3, wherein the measurement data comprises heart activity measurement data and the activity threshold is a heart activity threshold.

6. The method of claim 1, wherein the apparatus accumulates the total length of the detected one or more continuous sleep intervals and resumes accumulation after a time interval defined by the second threshold duration has passed from the latest detection of a restless sleep signal pattern.

7. The method of claim 1, wherein said computing the sleep quality metric further comprises:
computing a first sleep quality metric from the number of the detected one or more restless sleep signal patterns and a second sleep quality metric from the total length of the detected one or more continuous sleep intervals such that the first and second sleep quality metric are mapped to a common scale; and
computing the sleep quality metric as an average of the first sleep quality metric and the second sleep quality metric.

8. The method of claim 1, further comprising:
detecting a determined number of restless sleep signal patterns;
in response to said detecting, activating at least one sensor device to perform additional measurements on the user;
receiving additional measurement data from the at least one sensor device; and
processing the additional measurement data and estimating a physiological condition of the user on the basis of the additional measurement data.

9. The method of claim 1, further comprising:
estimating, on the basis of at least the sleep quality metric, an alertness metric indicative of a current or future alertness level of the user; and
outputting the alertness metric through the user interface.

10. The method of claim 9, further comprising:
determining that the alertness metric or the future alertness metric crosses a threshold level indicating a threshold alertness level; and
in response to said determining, outputting a notification of degrading alertness level to the user.

11. The method of claim 1, further comprising:
determining, from the measurement data the sleep start time and the sleep stop time; and
performing said detecting the one or more restless sleep signal patterns and detecting the one or more continuous sleep signal patterns only for a subset of the measurement data, the subset measured between the sleep start time and the sleep stop time.

12. The method of claim 11, wherein the sleep start time is detected by using a first sensor device and the measurement data used in the detection of the restless sleep signal patterns and the continuous sleep signal patterns is received from a second sensor device.

13. The method of claim 12, wherein the first sensor device is a photo sensor, and the sleep start time is detected by comparing light intensity sensed by the photo sensor with a light intensity threshold and, upon detecting that the sensed light intensity has remained below the light intensity threshold for a determined time interval, recording the sleep start time.

14. A computer system comprising:
at least one processor;
at least one memory storing a computer program code, wherein the at least one memory and the computer program code are configured, with the at least one processor, to cause the apparatus to perform operations comprising:
receiving measurement data measured by at least one sensor device during a time interval;
determining a sleep start time and a sleep stop time in the measurement data;
detecting from a subset of the measurement data, the subset measured between the sleep start time and the sleep stop time one or more restless sleep signal patterns indicating a restless sleep interval longer than a first threshold duration and computing a number of the detected one or more restless sleep signal patterns;
detecting, from the subset of the measurement data, one or more continuous sleep intervals not including any one of the one or more restless sleep signal patterns within a time interval longer than a second threshold duration and computing a total length of the one or more continuous sleep intervals;
computing a relation ratio of the total length of the detected one or more continuous sleep intervals to a duration from a sleep start time to a sleep stop time;
computing, on a basis of the computed relation ratio and the number of the detected one or more restless sleep signal patterns, a sleep quality metric indicating a quality of the user's sleep between the sleep start time and sleep stop time; and
outputting the sleep quality metric.

15. The apparatus of claim 14, wherein the operations further comprise causing the apparatus to accumulate the total length of the detected one or more continuous sleep intervals and to resume accumulation after a time interval defined by the second threshold duration has passed from the latest detection of a restless sleep signal pattern.

16. The apparatus of claim 14, wherein the apparatus computes the sleep quality metric by performing operations comprising:
computing a first sleep quality metric from the number of the detected one or more restless sleep signal patterns and a second sleep quality metric from the total length of the detected one or more continuous sleep intervals such that the first and second sleep quality metric are mapped to a common scale; and
computing the sleep quality metric as an average of the first sleep quality metric and the second sleep quality metric.

17. The apparatus of claim 14, wherein the operations further comprise:
detecting a determined number of restless sleep signal patterns;
in response to said detecting, activating at least one sensor device to perform additional measurements on the user;
receiving additional measurement data from the at least one sensor device; and
processing the additional measurement data and estimating a physiological condition of the user on the basis of the additional measurement data.

18. The apparatus of claim 14, wherein the operations further comprise:
estimating, on the basis of at least the sleep quality metric, an alertness metric indicative of a current or future alertness level of the users and
outputting the alertness metric through the user interface.

19. The apparatus of claim 18, wherein the operations further comprise:
determining that the alertness metric or the future alertness metric crosses a threshold level indicating a threshold alertness level; and
in response to said determining, outputting a notification of degrading alertness level to the user.

20. The apparatus of claim 14, wherein the operations further comprise:
determining from the measurement data the sleep start time and the sleep stop time;
performing said detecting the one or more restless sleep signal patterns; and
detecting the one or more continuous sleep signal patterns only for a subset of the measurement data, the subset measured between the sleep start time and the sleep stop time.

21. The apparatus of claim 20, wherein the operations further comprise:
detecting the sleep start time detected by using a first sensor device; and
receiving the measurement data used in the detection of the restless sleep signal patterns and the continuous sleep signal patterns from a second sensor device different from the first sensor device.

22. The method of claim 21, wherein the first sensor device is a photo sensor, the operations further comprising:
detecting the sleep start time by comparing light intensity sensed by the photo sensor with a light intensity threshold; and
upon detecting that the sensed light intensity has remained below the light intensity threshold for a determined time interval, recording the sleep start time.

23. A computer program product embodied on a non-transitory distribution medium and comprising a computer-readable program code that, when read and executed by a computer system, cause execution of a computer process comprising:
receiving measurement data measured by at least one sensor device during a time interval;
determining a sleep start time and a sleep stop time in the measurement data;
detecting from a subset of the measurement data, the subset measured between the sleep start time and the sleep stop time, one or more restless sleep signal patterns indicating a restless sleep interval longer than a first threshold duration and computing a number of the detected one or more restless sleep signal patterns;
detecting, from the subset of the measurement data, one or more continuous sleep intervals not including any one of the one or more restless sleep signal patterns within a time interval longer than a second threshold duration and computing a total length of the one or more continuous sleep intervals;
computing a relation ratio of the total length of the detected one or more continuous sleep intervals to a duration from a sleep start time to a sleep stop time;
computing, on a basis of the computed relation ratio and the number of the detected one or more restless sleep signal patterns, a sleep quality metric indicating a quality of the user's sleep between the sleep start time and sleep stop time; and
outputting the sleep quality metric.

* * * * *